United States Patent
Olmiere et al.

(10) Patent No.: US 10,881,638 B2
(45) Date of Patent: Jan. 5, 2021

(54) EYE HEALTH COMPOSITION

(71) Applicant: Laboratoires Thea, Clermont-Ferrand (FR)

(72) Inventors: Céline Olmiere, Vertaizon (FR); Fabrice Mercier, Clermont-Ferrand (FR)

(73) Assignee: LABORATOIRES THEA, Clermont-Ferrand (FR)

( * ) Notice: Subject to any disclaimer, the term of this patent is extended or adjusted under 35 U.S.C. 154(b) by 0 days.

(21) Appl. No.: 15/557,103

(22) PCT Filed: Mar. 25, 2016

(86) PCT No.: PCT/FR2016/050697
§ 371 (c)(1),
(2) Date: Sep. 10, 2017

(87) PCT Pub. No.: WO2016/151269
PCT Pub. Date: Sep. 29, 2016

(65) Prior Publication Data
US 2018/0042894 A1 Feb. 15, 2018

(30) Foreign Application Priority Data
Mar. 25, 2015 (FR) ...................................... 1552483

(51) Int. Cl.
| | | |
|---|---|---|
| *A61K 31/375* | (2006.01) | |
| *A61K 31/05* | (2006.01) | |
| *A61K 31/202* | (2006.01) | |
| *A61K 31/355* | (2006.01) | |
| *A61K 33/30* | (2006.01) | |
| *A61K 33/34* | (2006.01) | |
| *A61K 31/07* | (2006.01) | |
| *A61K 9/48* | (2006.01) | |
| *A61K 9/00* | (2006.01) | |
| *A61K 31/047* | (2006.01) | |

(52) U.S. Cl.
CPC .......... *A61K 31/375* (2013.01); *A61K 9/0053* (2013.01); *A61K 9/4858* (2013.01); *A61K 31/047* (2013.01); *A61K 31/05* (2013.01); *A61K 31/07* (2013.01); *A61K 31/202* (2013.01); *A61K 31/355* (2013.01); *A61K 33/30* (2013.01); *A61K 33/34* (2013.01)

(58) Field of Classification Search
CPC ...... A61K 31/355; A61K 33/30; A61K 33/34; A61K 31/375; A61K 31/185; A61K 35/60; A61K 9/0053; A61K 31/05; A61P 27/02; A61P 3/02; A23L 33/15; A23L 33/16
See application file for complete search history.

(56) References Cited

U.S. PATENT DOCUMENTS

| | | | | |
|---|---|---|---|---|
| 2005/0163873 A1* | 7/2005 | Ritch | ..................... | A61K 31/14 424/752 |
| 2007/0141138 A1* | 6/2007 | Feuerstein | ............... | A61K 9/48 424/451 |
| 2008/0181972 A1* | 7/2008 | Amico | ................. | A61K 31/352 424/655 |
| 2009/0226547 A1* | 9/2009 | Gilbard | ................ | A61K 31/353 424/729 |
| 2012/0058088 A1* | 3/2012 | Sardi | ..................... | A61K 31/05 424/93.7 |

FOREIGN PATENT DOCUMENTS

| | | |
|---|---|---|
| GB | 2483121 | 2/2012 |
| WO | WO 2016/151269 | 9/2016 |

OTHER PUBLICATIONS

Evans et al (Ophthalmic and Physiological Optics, 2014, vol. 34, pp. 390-396) (Year: 2014).*
Richer (Nutrients, online Oct. 2014, vol. 6, pp. 4404-4420) (Year: 2014).*
Taggart Are You Getting What You Need From Your AREDS Supplements?, BrightFocus Foundation, https://www.brightfocus.org/macular/news/are-you-getting-what-you-need-your-areds-supplements, downloaded in Aug. 2018 (Year: 2018).*
Rapport de Recherche Internationale et Opinion Ecrite de l'Administration Chargée de la Recherche Internationale [International Search Report and the Written Opinion] dated Jun. 29, 2016 From the International Searching Authority Re. Application No. PCT/FR2016/050697. (11 Pages).
Bonds et al. "Effect of Long-Chain Omega-3 Fatty Acids and Lutein + Zeaxanthin Supplements on Cardiovascular Outcomes. Rsults of the Age-Related Eye Disease Study 2 (AREDS2): Randomized Clinical Trial", JAMA Internal Medicine, XP002751613, 174(5): 763-771, May 2014.
Nagineni et al. "Resveratrol Suppresses Expression pf VEGF by Human Retinal Piginent Epithelial Cells: Potential Nutraceutical for Age-Related Macular Degeneration", Aging and Disease, XP055232237, 5(2): 88-100, Apr. 2014. p. 94-96.
Pournaras et al. "Regulation of Retinal Blood Flow in Health and Disease", Progress in Retinal and Eye Research, 27(3): 284-330, Published Online Feb. 23, 2008.
"Eye Vitamins developed by Fortifeye Vitamins", Fortifeye Vitamin Difference, printed Dec. 24, 2019 from https://eyevitamin.net/2012/12/29/eye-vitamins-developed-by-fortifeye-vitamins/.
"New Supplement Family includes Important Antioxidants, Including Green Tea, Spinach, Blueberry Lutein, Lycopene and Resveratrol", Business Wire, Dec. 4, 2006.
Dr. Michael Lange Links Ocular and Overall Health, Fortifeye Vitamins, printed Dec. 24, 2019 from https://www.fortifete.com/dr-michael-lange-anti-aging/dr-michael-lange-links-ocular-and-overall-health/#more-1836.

(Continued)

*Primary Examiner* — Mark V Stevens
(74) *Attorney, Agent, or Firm* — Knobbe, Martens, Olson & Bear LLP

(57) ABSTRACT

Ophthalmic nutraceutical composition comprising:
vitamins;
trace elements;
carotenoids;
omega-3 fatty acids; and
resveratrol.

5 Claims, 5 Drawing Sheets

(56) References Cited

OTHER PUBLICATIONS

Fortifeye Complete Macular Defense, Fortifeye Vitamins, printed Jan. 9, 2020 from www.fortifeye.com/products/fortifeye-complete-macular-defense.

Fortifeye Complete Plus, Fortifeye Vitamins, printed Jan. 9, 2020 from www.fortifeye.com/products/fortifeye-complete-plus-multivitamin/.

Fortifeye Super Omega-3 Fish Oil, Fortifeye Vitamins, printed Sep. 1, 2020 from www.fortifeye.com/products/fortifeye-super-omega-3-fish-oi/.

Fortifeye Zinc Free Macular Defense, Fortifeye Vitamins, printed Jan. 9, 2020 from www.fortifeye.com/products/fortifeye-zinc-free-macular-defense-will-be-availableend-of-september.

Klepsch, "Substantial Equivalence Opinion for Resveratrol", Food Safety Authority of Ireland, Jan. 11, 2012.

Lange, "Food for macular Degeneration", Macular degeneration treatment in Ocala, printed Sep. 12, 2019 from http://maculardegenerationtreatmentinocala.wordpress.com/2012/02/03/food-for-macular-degeneration/.

New technology and proper nutrition may decrease vision loss from macular degeneration, Eye Vitamins, printed Jul. 1, 2020 from https://eyevitamin.net/2014/05/26/new-technology-and-proper-nutrition-may-decrease-vision-loss-from-macular-degeneration/.

Reagan-Shaw et al., "Dose translation from animal to human studies revisited", The FASEB Journal, vol. 22, pp. 659-661, Mar. 2007.

Rossi et al., "trans-Resveratrol in Nutraceuticals: Issues in Retail Quality and Effectiveness", Molecules 2012, 17, 12393-12405, Oct. 22, 2012.

\* cited by examiner

EYE HEALTH COMPOSITION

RELATED APPLICATIONS

This application is a National Phase of PCT Patent Application No. PCT/FR2016/050697 having International filing date of Mar. 25, 2016, which claims the benefit of priority of French Patent Application No. 1552483 filed on Mar. 25, 2015. The contents of the above applications are all incorporated by reference as if fully set forth herein in their entirety.

FIELD AND BACKGROUND OF THE INVENTION

The present invention proposes a nutraceutical ophthalmic composition particularly for the improvement of eye health and the prevention of eye diseases. Such composition comprises vitamins, trace elements, carotenoids, omega-3 fatty acids and resveratrol.

Surprisingly, the present application demonstrates better efficacy and a synergistic effect of the resveratrol in such an association, both in the treatment of pathological retinal cells as well as in maintaining and improving the health of healthy cells.

Age-related macular degeneration (AMD) is the primary cause of visual impairment in people over 50 years old. All forms combined, this disease affects about 8% of the French population, but the frequency thereof increases significantly with age: it affects 1% of people from 50 to 55 years, about 10% from 65 to 75 years and 25% to 30% of those over 75 years. If only the late forms of the disease are taken into account, associated with a loss of central vision, these figures are divided by about two. But in years to come, because of extended life expectancy, the incidence of AMD is not going to stop increasing.

This pathology selectively affects the macular region, i.e., the central area of the retina, causing progressive loss of central vision which is the field of vision used for reading, recognizing faces or driving. It is the primary cause of visual impairment in older subjects.

The disease begins in an early phase, without degeneration, called age-related maculopathy (ARM or "early dry"). This phase is characterized by the accumulation of small whitish deposits (or "soft drusen") within and around the macula. These deposits are visible during a simple examination of the fundus of the eye. This phase is most often asymptomatic, but the patient can possibly perceive deformations of straight lines ("metamorphopsia") and fuzzy spots.

Indeed, upon examining the fundus of the eye, the ophthalmologist observes white spots (drusen) or irregularities of the deepest layer of the retina, characteristic signs of AMD in someone more than 50 years old. When an examination of the fundus of the eye is performed at a more advanced stage, there is evidence of more evolved lesions, such as alterations to the pigmentary epithelium, hemorrhages or deposits of liquids, also called exudates.

In the more advanced stages, symptoms appear, that vary depending upon the seriousness of the disease:
  Loss of visual acuity, with the need to have better lighting for reading or for any precision work;
  Central vision more and more fuzzy, alteration of perception of colors, distortion of straight lines, which appear deformed and wavy;
  Appearance of a dark spot in the center of the visual field called scotoma, difficulties in recognizing faces, visual hallucinations or abrupt loss of visual acuity;
  Serious impact on the second eye varies greatly from one person to another: it may occur quickly, within a year, within 10 years, or never. If an exudative AMD is present in one eye, there is a risk of it being developed in the other eye.

An ARM can remain stable for life. However, in about half of the cases, and under the influence of various factors, ARM develops into late degenerative forms:
  Atrophic form, which is a dry form, also called atrophic form, wherein the macula atrophies during aging and is progressively replaced by scar tissue; or
  Wet form, which is an exudative form wherein small vessels filled with blood develop beneath the macula. Bleeding easily, these new blood vessels are responsible for exudates and hemorrhages of the fundus of the eye.

These two late forms have a more or less equal incidence. They lead to an irreversible deterioration of the macula and to a loss of central vision affecting one or both eyes. Mixed forms can be observed.

The wet form of AMD, called neovascular or exudative, just like diabetic retinopathy, macular edema, retinal venous occlusion or acute myopia, results in a proliferation of abnormal new vessels beneath the retina. These fragile vessels allow serum to be diffused, which is responsible for lifting of the retina, and/or of blood causing the appearance of retinal hemorrhages. This form develops quickly if it is not cared for, with a loss of vision within a few weeks or even a few days. This process can be slowed by anti-VEGF type medications.

Thus, since 2006, the wet form of AMD has been treated with VEGF inhibitors. Progressively, other neovascular pathologies (macular edema, retinal venous occlusion or acute myopia) are also treated by these treatments. VEGF is a growth factor that allows for the formation of new blood vessels. The blockage thereof by repeated injections of anti-VEGF, directly into the eye by intravitrial administration at the rate of an average of seven injections per year, makes it possible to stop the progress of the disease. Currently there are three VEGF inhibitors:
  pegaptanib since 2006, considered to have little effect;
  ranibizumab since 2007, with about 30% unresponsive or no longer responsive to the treatment; and
  aflibercept since 2012.

These anti-VEGF have largely replaced the former techniques intended to destroy the new vessels, particularly photocoagulation (thermal destruction of abnormal vessels) and photodynamics. This latter technique, dating from the early 2000s, consists of an intravenous injection of a photosensitive product (verteporfin) which becomes toxic under the effect of red light applied locally by means of a laser.

Prior to these serious pharmaceutical treatments, performed at advanced stages of the pathology, studies were performed in an attempt to find earlier and "lighter" approaches, for the purpose of preventing the progress of the disease.

Thus, studies called AREDS 1 & 2 (*Age-Related Eye Disease Study*) were performed in order to demonstrate the beneficial effect of food supplements on eye diseases.

These studies have revealed that antioxidant-based food supplements are potentially capable of preventing the development of eye diseases, particularly those relating to age, and especially AMD.

In practice, the AREDS 1 study recommended the administration of antioxidants daily in the form of trace elements and vitamins, as follows:

| | |
|---|---|
| Zinc | 80 mg |
| Vitamin C | 500 mg |
| Vitamin E | 267 mg |
| Copper | 2 mg |
| Beta-carotene (= Vitamin A) | 15 mg |

Moreover, the AREDS 2 study recommended removing Vitamin A and reported the benefit of taking daily carotenoid supplements (macular pigments) and omega-3 fatty acids, as follows:

| | |
|---|---|
| Lutein | 10 mg |
| Zeaxanthin | 2 mg |
| docosahexaenoic acid (DHA) | 350 mg |
| eicosapentaenoic acid (EPA) | 650 mg |

Based on the results of the AREDS studies, therefore, it is recommended that food supplements be taken daily by people with a high risk of developing AMD, particularly in patients having an ARM in one or both eyes, as well as in patients with advanced AMD still only involving one eye.

The article "*Effect of long-chain ω-3 fatty acids and lutein+ zeaxanthin supplements on cardiovascular outcomes*" from the AREDS 2 research group (*JAMA Intern Med.* 2014; 174(5):763-771) describes the absence of effects of this type of food supplement on cardiovascular pathologies, when they are administered to patients with AMD. In any event, this study in no way describes the effect of administered supplements on AMD or on eye health in general.

However, there is an evident need to develop solutions for providing better care particularly of AMD, both with respect to prevention as well as the treatment thereof.

SUMMARY OF THE INVENTION

According to a first aspect, the present invention seeks a nutraceutical ophthalmic composition comprising:
vitamins;
trace elements;
carotenoids;
omega-3 fatty acids; and
resveratrol.

Within the context of the invention, what is called a "nutraceutical composition" is a composition the purpose of which is to supplement the normal dietary regime and constituting a concentrated source of nutrients or other substances having a nutritional or physiological effect, alone or in combination. Advantageously, it involves a dietary supplement.

Within the context of the invention, what is called an "ophthalmic composition" is a composition having beneficial properties for eye health. However, this does not exclude the possibility that such a composition has a beneficial effect on other organs in humans or animals.

In the present application, it is shown that the combination of different listed compounds has a beneficial action in modulating both the level of expression (quantitative modification) as well as the phosphorylation/activity (qualitative modification) of the receptors to vascular endothelial growth factor (VEGF), hereinafter denoted VEGFR.

According to a first variant, the composition according to the invention is made up of the ingredients listed above.

Advantageously, the vitamins, trace elements, omega-3 fatty acids and carotenoids ingredients, known for their antioxidant properties, are chosen as recommended by the AREDS Studies.

According to a particular embodiment, the composition according to the invention comprises at least one vitamin, advantageously a combination of vitamins. Advantageously it involves vitamin C and/or vitamin E.

It can also involve the following vitamins:
nicotinamide or niacinamide or vitamin B3 or PP;
pyridoxine, for example in the form of pyridoxine HCl, or vitamin B6;
riboflavin or vitamin B2;
thiamine, for example in the form of thiamine nitrate, or vitamin B1;
cyanocobalamin or vitamin B12;
folic acid or vitamin B9;
Vitamin B5;
Vitamin B 8;
Vitamin D.

Vitamin C, available in the form of ascorbic acid or calcium ascorbate, is advantageously present in a quantity (daily dose) of between 50 and 500 mg, for example equal to 240 mg or 120 mg.

Vitamins E or alpha-tocopherol, available in oil form at 67% for example, is advantageously present in a quantity (daily dose) of between 10 and 500 mg, for example equal to 30 mg.

According to another embodiment, the following daily quantities expressed in milligrams can be envisaged for the following vitamins:
vitamin B3 or PP: 1 to 100, for example 18;
Vitamin B6; 1 to 10, for example 2;
Vitamin B2; 1 to 10, for example 1.6;
Vitamin B1; 1 to 10, for example 1.4;
Vitamin B12; 0.0005 to 0.01, for example 0.001;
Vitamin B9; 0.1 to 1, for example 0.2.

According to a particular embodiment, the composition according to the invention does not comprise vitamin A or beta-carotene.

According to a particular embodiment, the composition according to the invention comprises at least one trace element, advantageously a combination of trace elements. It advantageously involves zinc (Zn) and/or copper (Cu). It can also involve the following trace elements:
manganese, for example anhydrous manganese sulfate;
selenium, for example sodium selenite;
magnesium, for example magnesium oxide.

Zinc (Zn), available in the form of zinc oxide or zinc sulfate (monohydrate), is advantageously present in a quantity (daily dose) of between 5 and 100 mg, for example equal to 12.5 mg.

Copper (Cu), available in the form of copper sulfate, monohydrate or anhydrous, is advantageously present in a quantity (daily dose) of between 0.2 and 10 mg, for example equal to 1 mg.

According to another embodiment, the following daily quantities expressed in milligrams can be envisaged for the following trace elements:
manganese: between 1 and 10 mg, for example 1 mg;
selenium: between 0.01 and 0.1 mg, for example 0.025 mg;
magnesium: between 1 and 50 mg, for example 10 mg.

According to a particular embodiment, the composition according to the invention comprises at least one carotenoid, advantageously a combination of carotenoids. It advantageously involves lutein and/or zeaxanthin. It can also involve the following carotenoids:
- meso-zeaxanthin;
- lycopene;
- astaxanthin.

Lutein, available in the form of 20% lutein by weight, is advantageously present in the quantity (daily dose) of between 2 and 50 mg, for example equal to 10 mg.

Zeaxanthin, available in the form of 5% or 14% zeaxanthin by weight, is advantageously present in a quantity (daily dose) of between 0.5 and 10 mg, for example equal to 2 mg.

According to a particular embodiment, the composition according to the invention comprises at least one omega-3 type polyunsaturated fatty acid, advantageously a combination of omega-3 fatty acids. Advantageously it involves eicosapentaenoic acid (EPA) and/or docosahexaenoic acid (DHA). It can also involve the following omega-3 fatty acids:
- alpha linolenic acid (ALA);
- docosapentaenoic acid (DPA).

The omega-3 fatty acids used within the scope of the composition according to the invention can be in the form of fish oil, for example fish oil of 70% by weight of omega-3 fatty acids, or vegetable oils, for example flax. These fatty acids are advantageously present in a quantity (daily dose) of between 500 and 1000 mg, for example equal to 665 mg, which represents 950 mg fish oil. More generally, fish oil can be present in a daily quantity of between 500 and 1000 mg.

In this context, EPA is advantageously present in a quantity (daily dose) of between 100 and 1000 mg, for example equal to 380 mg or 172 mg.

In this context, DHA is advantageously present in a quantity (daily dose) of between 100 and 1000 mg, for example equal to 190 mg or 366 mg.

In this context, DPA is advantageously present in a quantity (daily dose) of less than 100 mg, even 50 mg.

Characteristically, the composition according to the invention further comprises resveratrol.

Of course, resveratrol has been described in the article by Nagineni et al. (*Aging and Disease*, 2014; 5(2): 88-100) as inhibiting in vitro the overexpression of VEGF induced by cytokines in human retinal pigmentary epithelium cells (HRPE cells). However, no effect on VEGF growth factor receptors (VEGFR) is described. Although the article alludes to a potential nutraceutical interest of this compound with respect to AMD, it in no way teaches that a synergistic effect on the expression of VEGFR can be obtained when resveratrol is combined with other compounds.

Resveratrol is a polyphenolic compound, derived from stilbene, of the formula:

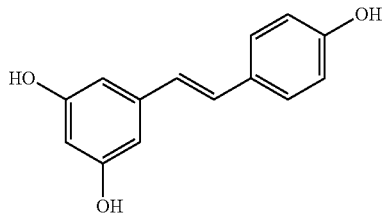 [SMILES: Oc1ccc(/C=C/c2cc(O)cc(O)c2)cc1]

There are two isomers, but the trans form is predominantly active. In the description that follows, the term "resveratrol" may therefore be used instead and in place of trans-resveratrol.

Resveratrol is a polyphenol found in abundant quantities in certain fruits, particularly in grapes and oilseeds, and in wine. There are currently various commercial sources of resveratrol that can be used for the preparation of a compound according to the invention:
*Vitis vinifera:*
Grape skin
Grape seed
*Polygonum Cuspidatum*
Product by fermentation
Preferred sources are in particular:
Resveratrol 5% source *Vitis vinifera*, grape skin (PHARMANAGER INGREDIENT);
Resveratrol 98% source *Vitis vinifera*, grape skin (CAMBRIDGE COMMODITIES; CAS Number: 501-36-0).

Resveratrol is advantageously present in a quantity (daily dose) equal to or greater than 1 mg, even 2 mg, 5 mg, 10 mg, 20 mg, 30 mg, 50 mg, 60 mg and even 100 mg or 200 mg. According to a particular embodiment, the daily quantity thereof is equal to or greater than 20 mg or even greater than 20 mg, equal to or greater than 30 mg or even greater than 30 mg, even equal to or greater than 50 mg, even equal to or greater than 60 mg, even equal to or greater than 100 mg. Advantageously, it is less than or equal to 1 g, preferably less than or equal to 500 mg, and in a particularly preferred manner, less than or equal to 200 mg. According to a particular embodiment, the composition according to the invention comprises a daily dose of resveratrol equal to 50 mg, 60 mg, 70 mg, 80 mg, 90 mg, 100 mg, 150 mg or 200 mg.

To the Applicant's knowledge, it has already been recommended to use resveratrol in compositions, including for ophthalmic purposes, due to the properties thereof that have previously been described: antioxidant, anti-apoptotic, anti-tumorigenic, anti-inflammatory, anti-angiogenic and vasorelaxant.

Thus, the application US 2005/0163873 proposes treating the neurodegenerative component of glaucoma with compositions having a protective effect with respect to nerve cells damages. This document establishes a list of compounds that can be used in this context, one of which is resveratrol. Neuroprotective compositions can contain resveratrol in combination with various other compounds. The daily dose of resveratrol that could be administered is not explicitly indicated.

However, the present application provides evidence of the following new effects:
- A beneficial or at least non-deleterious effect on healthy cells;
- An anti-VEGF activity, both quantitative and qualitative, in diseased cells, boosted in the presence of other ingredients of a composition according to the invention, in particular in the context of an AREDS formulation.

According to another embodiment, the composition according to the invention can contain other active ingredients such as:
- one or more polyphenol(s), such as epigallocatechin-3-gallate (EGCG);
- glutathione, in the amount of 1 to 10 mg per day, even 2 mg per day;
- one or more anthocyanoside(s);
- hydroxythyrosol.

The content of each of these ingredients is easily determined and adjusted by a person skilled in the art.

Thus, and according to one variant, the composition comprises or is composed of the following ingredients:

vitamin C;
vitamin E;
zinc;
copper;
lutein;
zeaxanthin;
omega-3 fatty acids from fish oil, particularly EPA and DHA;
resveratrol.

According to another variant, the composition comprises or is composed of the following ingredients, on the basis of a daily dose:
- 50 mg to 500 mg of vitamin C, advantageously 240 mg, and particularly advantageously 120 mg;
- 10 mg to 500 mg of vitamin E, advantageously 30 mg;
- 5 mg to 100 mg of zinc, advantageously 12.5 mg;
- 0.2 mg to 10 mg of copper, advantageously 1 mg;
- 2 mg to 50 mg of the lutein, advantageously 10 mg;
- 0.5 mg to 10 mg of zeaxanthin, advantageously 2 mg;
- 100 mg to 1000 mg of EPA, advantageously 380 mg, particularly advantageously 172 mg;
- 100 mg to 1000 mg of DHA, advantageously 190 mg, particularly advantageously 366 mg;
- resveratrol, advantageously in a quantity of more than 20 mg, preferably more than 30 mg, particularly preferably more than 50 mg, very advantageously in a quantity equal to or greater than 60 mg.

According to a preferred embodiment, the composition of the invention comprises or is composed of the following ingredients, based on a daily dose:
- 120 mg vitamin C;
- 30 mg vitamin E;
- 12.5 mg zinc;
- 1 mg copper;
- 10 mg lutein;
- 2 mg de zeaxanthin;
- 172 mg EPA;
- 366 mg DHA;
- resveratrol, advantageously in a quantity of 50 mg, very advantageously in a quantity equal to or more than 60 mg.

According to an advantageous embodiment, said composition is formulated in 2 capsules, each containing the ingredients listed above, but in one half of the quantity.

According to a first alternative, all of said ingredients are mixed and administered in a single composition. Alternatively, said ingredients can be combined in different ways in order to be formulated and/or administered simultaneously or staggered over time.

According to a particular embodiment, the composition according to the invention is lacking at least one of the ingredients from the following list:
- saffron;
- a metals chelating agent, such as EDTA or phytic acid;
- a nucleotide;
- pycnogenol;
- a Ginkgo Biloba extract.

According to this embodiment, the composition used does not combine resveratrol with saffron, or resveratrol with a metals chelating agent and one or more nucleotides, or resveratrol and pycnogenol and/or a Ginkgo Biloba extract.

The document GP 2483121 describes compositions that systematically comprise a combination of resveratrol and saffron, and teaches that these two compounds have a beneficial synergistic effect on the progress of age-related pathologies, particularly AMD. In this document, saffron is indicated as known, in isolation, for having an effect on AMD. As regards resveratrol, it is presented as having general anti-aging virtues, which derive from the antioxidant and anti-inflammatory properties thereof.

According to a particular aspect, the invention concerns a nutraceutical ophthalmic composition comprising:
- vitamins;
- trace elements;
- carotenoids;
- omega-3 fatty acids; and
- resveratrol in a quantity of more than 20 mg;
- said composition not comprising saffron,
- and the use of such composition as food supplement in ophthalmology.

The composition according to the invention is advantageously intended for oral administration.

It can be in liquid, solution, suspension, paste or gel form.

Advantageously, it is in solid form, such as powder, tablets including effervescent tablets, capsules, gel caps, tablets or pills, prepared conventionally with the aid of acceptable additives such as binding agents, fillers, lubricants, breakdown agents or wetting agents. The tablets can optionally be coated in a manner known to a person skilled in the art, with sugars, films or enteric coatings.

Alternatively, other delivery systems can be used, such as preparations in soft gelatin or gelatin based capsules or formulations prepared by virtue of nanotechnologies, such as nano-dispersions, nano-emulsions or nano-encapsulations.

Moreover, the composition according to the invention can contain one or more additives such as colorants, pigments, fragrances, etc.

According to one particular embodiment, the composition is in the form of capsules, defining a given volume wherein the composition is contained. The capsule is broken down in the digestive system in order to release the active ingredients and allow their assimilation by the body.

In a manner known to a person skilled in the art, the distribution in this type of packaging requires a compromise between:
- a limited number of doses, to ensure good compliance with treatment;
- a volume adapted to doses, allowing the formulation of all of the ingredients and easy ingestion.

In the present case, a composition according to the invention preferably is in the form of one or more capsules, advantageously 2 capsules. Thus, said capsules can be taken with a little water before or during the main meal. Preferably, the composition according to the invention is administered daily, for example once per day.

In this context, conventional additives are:
- glycerol, for example glycerol monostearate; and/or
- soy oil; and/or
- beeswax; and/or
- soy lecithin.

Appropriately, said additives are added to a composition according to the invention insofar as they are capable of improving, for example, the flow or homogenization properties thereof.

Moreover, and in a manner known to a person skilled in the art, the jacket of the capsules can be prepared from the following ingredients:
- gelatin; and/or
- red iron oxide; and/or
- black iron oxide; and/or
- sorbitol; and or
- glycerol.

Within the scope of the present invention, it was determined that the anti-VEGF activity of resveratrol could be improved, both for inhibition of the expression of receptors as well as for their phosphorylation, by the presence of other ingredients, in this instance vitamins, trace elements, carotenoids and omega-3 fatty acids, which are not known for this property. Remarkably, this effect is dose-dependent.

Thus, the composition according to the invention is of obvious interest for use in the treatment of eye pathologies associated with an overexpression or overproduction of the VEGF/VEGFR pathway (VEGF receptors), such as AMD, in particular exudative, retinal venous occlusion, macular edema, diabetic macular edema, myopia, diabetic retinopathy, neovascular glaucoma or corneal neovascularization.

According to another aspect, the present invention concerns a composition as defined above for use in:
- maintaining or improving eye health; and/or
- prevention of eye diseases; and/or
- modulation of the expression and/or of the activity of the VEGF receptors (VEGFR) of the eye cells, such as retinal cells or those of the anterior segment (corneal).

Although the anti-VEGF effect of resveratrol on retinal cells was known, it was feared that the use thereof on healthy cells could have a comparable effect, possibly harmful to eye health (Pournaras et al., *Progress in Retinal and Eye Research* 27 (2008) 284-330). Now, within the context of the present application, it has been shown that a composition according to the invention comprising resveratrol not only had an anti-VEGF effect on pathological cells, but contrary to what was expected by a person skilled in the art, it had a non-deleterious and even beneficial effect on undamaged cells.

Thus, and in particular, a composition according to the invention can be beneficially administered to a subject presenting at least some symptoms of the pathologies listed above only in one eye. Unexpectedly, the composition according to the invention makes it possible to treat not only the diseased eye but presents no risk for the undamaged eye, and even makes it possible to ensure or prolong the good health thereof.

Thus, the invention preferably concerns the composition according to the invention for the above-mentioned uses, characterized in that it is used in a subject affected by symptoms of the pathology only in one eye, a healthy subject, or a young subject at risk.

According to another aspect, the present invention concerns a method for maintaining and/or improving eye health in a subject, consisting in orally administering a composition according to the invention.

Within the context of the invention, the terms "subject" and "patient" can be used interchangeably.

Advantageously, the subject is a healthy subject, for whom an ophthalmological examination reveals no characteristic signs of eye pathologies, particularly AMD or ARM. Again, more advantageously, it involves a subject called "young", i.e., younger than 50 years, even younger than 45 years. According to a particular embodiment, it involves a young subject called "at risk," i.e., presenting characteristics or history associated with an increased risk of developing an eye pathology, in particular an AMD or an ARM. The currently identified risk factors are in particular:
- smoker;
- hereditary genetic risk;
- high blood pressure;
- obesity;
- cataract operation;
- myopia;
- diabetes.

According to another aspect, the present invention concerns a method for preventing eye diseases in a subject, consisting of administering orally a composition according to the invention.

Advantageously, the eye diseases concerned are age-related diseases, in particular retinal damage, and more specifically neovascular retinal pathologies such as exudative AMD.

Preferably, the subject is a healthy subject as defined above, or a subject affected by some of these signs only in one eye.

According to another aspect, the present invention concerns a method for modulating the expression and/or activity of the VEGFR receptors of eye cells in a subject, consisting of administering orally a composition according to the invention. As shown in the present application, the modulation corresponds to an inhibition in the presence of diseased cells, particularly within the context of retinal damage, while it corresponds to a preservation and even stimulation or activation in the presence of healthy cells. According to a particular embodiment, the subject is one who is suffering from an ophthalmic pathology, in particular neovascular, for example AMD (advantageously exudative), retinal venous occlusion, macular edema, diabetic macular edema, myopia, diabetic retinopathy, neovascular glaucoma or corneal neovascularization.

According to a preferred embodiment, the composition comprising resveratrol according to the invention is an AREDS type formulation associating other active ingredients, as described above.

As has been already mentioned, according to studies performed by the Applicant, the composition according to the invention can encourage the maintenance of healthy retinal cells in good health, while it contributes to eliminating pathological retinal cells. Thus, such a composition can be recommended in the case of patients suffering from an ophthalmic pathology, in particular neovascular, as listed above, or suffering from such a pathology in only one eye.

In addition to this beneficial effect in the case of a detectable or reported pathology, the composition according to the invention can be used to maintain or stimulate the expression and/or activity (phosphorylation) of the VEGF receptors (VEGFR) of healthy eye cells, particularly retinal cells. This results in good neovascularization, and thus could provide good blood irrigation with an increased contribution of essential nutrients for the cells, so as to maintain them in good health and prevent diseases, particularly age-related diseases.

A target population is therefore comprised of subjects for whom an ophthalmological examination reveals no characteristic signs of a neovascular eye pathology. As was already mentioned, it can involve so-called "young" individuals, namely 50 years old and younger, even younger than 45 years. In particular, it can involve so-called "at risk" individuals, having at least one of the following characteristics:
- smoker;
- hereditary genetic risk;
- high blood pressure;
- obesity;
- cataract operation;
- myopia;
- diabetes.

EMBODIMENTS OF THE INVENTION

The invention and the advantages deriving therefrom will be better understood from the following figures and examples in order to provide a non-limiting illustration of the invention.

DESCRIPTION OF SPECIFIC EMBODIMENTS OF THE INVENTION

I/COMPOSITION ACCORDING TO THE INVENTION

I-1/Formula of the Composition (A)

TABLE 1

Figure 1A:
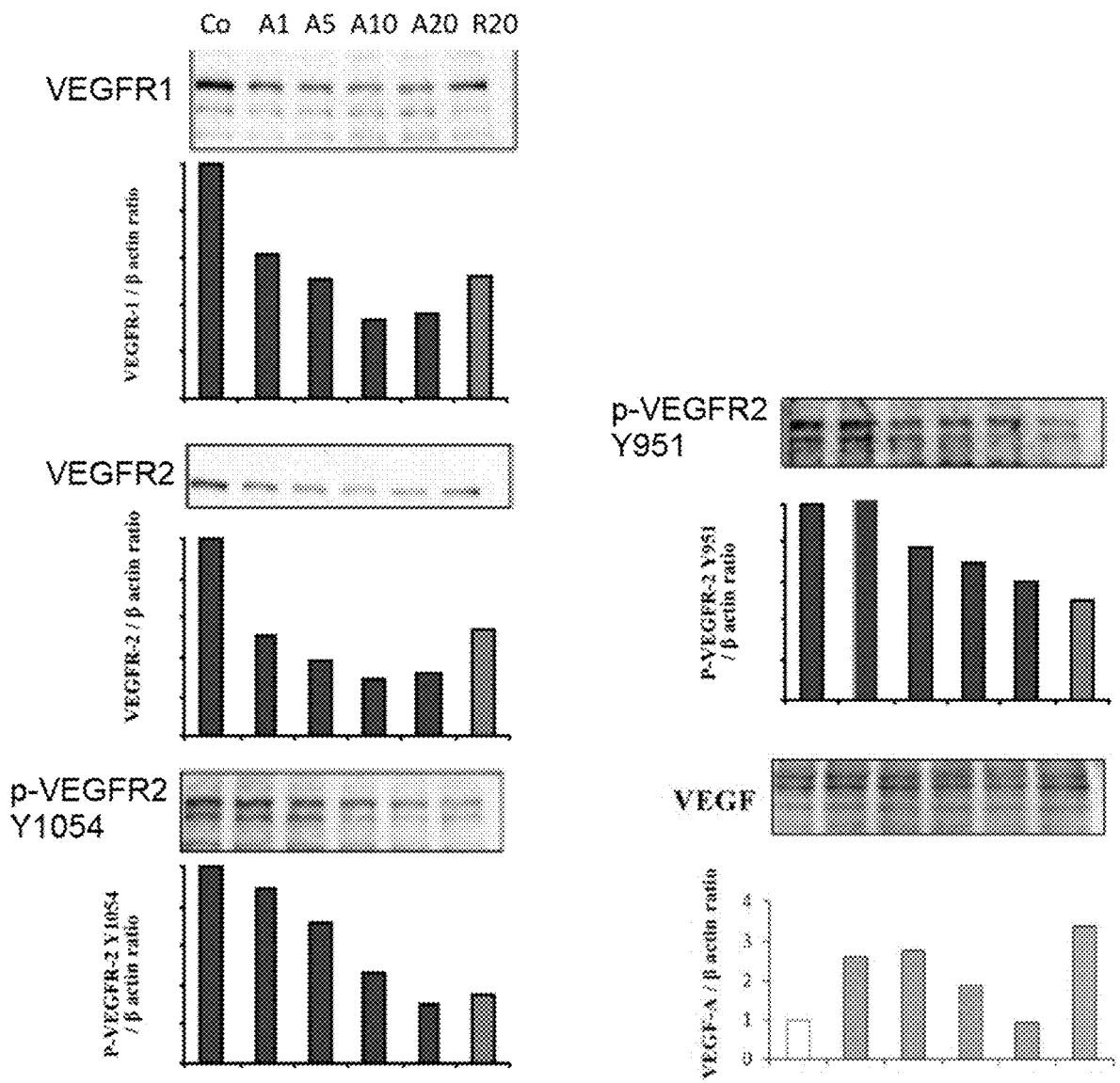
FIGS. 1A and 1B compare, in undifferentiated (pathological) retinal cells incubated (A) in the presence of a composition according to the invention (formula A) or (B), and in the presence of a composition similar to the one of the invention but without resveratrol (formula B), the expression of VEGFR receptors (VEGFR1 and VEGFR2) and their phosphorylation state (p-VEGF2 Y1054 and Y951), as well as VEGF, by western blot (image) and normalization by β-actin (diagram).

| formula of a composition according to the invention (A) | |
| --- | --- |
| Ingredient Quantity (mg)/day | Quantity (mg)/day |
| Vitamin C | 240 |
| Vitamin E | 30 |
| Zinc | 12.5 |
| Copper | 1 |
| Lutein | 10 |
| Zeaxanthin | 2 |
| Fish oil* | 950 |

TABLE 1-continued

| formula of a composition according to the invention (A) | |
| --- | --- |
| Ingredient Quantity (mg)/day | Quantity (mg)/day |
| DHA content | 190 |
| EPA content | 380 |
| Resveratrol. | 30 |

*Fish oil comprising 70% by weight omega-3 fatty acid including EPA and DHA.

I-2/Producing the Composition in the Form of Capsules

The quantities shown in table 1 correspond to a daily dose. In practice, the composition according to the invention is produced in the form of 2 capsules.

For each capsule, the following are added to the master batch:
glycerol monostearate;
beeswax;
soy lecithin.

The composition of the capsule jacket is as follows:
bovine gelatin
red iron oxide;
black iron oxide.

The capsules are then covered with a PVC/PVDC shell and an aluminum film. Alternatively, they can be packaged in a pill organizer.

It is recommended that these two capsules be taken with a little water before or during the main meal.

II/IN VITRO STUDY OF THE COMPOSITION ACCORDING TO THE INVENTION (FORMULA A)

II-1/Preparation of Solutions in Different Concentrations of Resveratrol

The stock solution is prepared in DMSO (Dimethyl Sulfoxide), in the amount of 0.115 g of formula A in 1 mL of DMSO, which corresponds to 10 mM of resveratrol.

Solutions of 1, 5, 10 and 20 µM resveratrol equivalent, denoted A1, A5, A10 and A20 respectively, are prepared from this stock solution. The dilutions are performed in a culture medium composed of DMEM/F12+1% FBS (fetal bovine serum without phenol red).

II-2/Effect of the Composition According to the Invention on Pathological Cells A/Protocol:
Cells studied: culture of undifferentiated ARPE-19 (ATCC® CRL-2302™) (human retinal pigment epithelium) cells.

These cells can be equated with damaged or pathological retinal cells.

Experimental Protocol:
a) Cell Culture:
The cells were maintained at 37° C., and in the presence of 5% $CO_2$ in the medium DMEM/F12 (GIBCO; 31331), completed with 10% FBS (Lonza) and 15 mM HEPES (pH 7.4; GIBCO).
b) Incubation Between the Compositions (Formula A or B) and the Cells: 1, 5, 10 or 20 µM. The 10 µM of Resveratrol Corresponding to 0.115 mg/mL of Formula A in DMEM/F12+1% FBS w/o Phenol Red.

The 10 μM equivalent from formula B also corresponding to 0.115 mg/mL of formula B in DMEM/F12+1% FBS w/o phenol red.

The day prior to treatment, the medium was eliminated and replaced by DMEM/F12 without phenol red (GIBCO; 21041), completed with 1% FBS (Lonza) and 15 mM HEPES (pH 7.4; GIBCO). After 24 hours, the cells were processed for 24 h with the different formulas (Formula A, Formula B and resveratrol) in the medium DMEM/F12 without phenol red (GIBCO; 21041), completed with 1% FBS (Lonza) and 15 mM HEPES (pH 7.4; GIBCO).

c) Western Blot:

After 24 h of stimulation, the media were eliminated, the cells were washed with PBS 1× then scrubbed in PBS 1×. The cells were centrifuged and the remainder was resuspended in the RIPA buffer along with a cocktail of protease inhibitors (Roche) and phosphatase inhibitors. The cells were lysed in ice for 30 minutes, then centrifuged. The protein concentration was determined by means of a protein quantification kit (Lowry kit, biorad). 45 μg of proteins were mixed with an equal volume of concentrated Laemmli 5×, denatured then loaded onto an acrylamide gel. After electrophoresis, the proteins were transferred to a nitrocellulose membrane (Amersham). The blots were then blocked with milk at 5%+ PBS-T 0.1% for 1 hour at ambient temperature. After blocking, the membranes were incubated with cell-signaling primary antibodies (VEGFR-1, VEGFR-2 (55B11) or Phospho-VEGF Receptor 2 (Tyr951) (15D2)) or Abcam (Anti-VEGF antibody [VG-1]). The membranes were washed 3 times with 0.1% PBS-T then incubated with corresponding HRP conjugated antibodies for 1 hour at ambient temperature. The membranes were again washed 3 times in 0.1% PBS-T and the signal was detected by ECL (Tebu bio). The images were recorded with the ChemiDoc imaging system and analyzed with Quantity One Software (Biorad) software.

d) Quantification of the Level of Expression and Activity of the Receptors:

The β-actin was also quantified in order to relativize the levels of expression.

e) Controls:

Co=control sample corresponding to DMSO (used for solubilization of the formulae) in the culture medium.

R20=Resveratrol at 20 μM alone diluted in the culture medium (=DMEM/F12+1% FBS (fetal bovine serum without phenol red).

B/Results:

1) Evidence of the Effect of the Resveratrol

To provide evidence of the effect of resveratrol on the expression of the VEGFR receptors, the composition according to the invention (formula A) is compared to a composition characterized by the absence of resveratrol, formula B given in table 2 below:

TABLE 2 composition of formula B without resveratrol

| Ingredient | Quantity (mg) |
|---|---|
| Vitamin B1 | 1.4 |
| Vitamin B2 | 1.6 |
| Vitamin B3 | 18 |
| Vitamin B6 | 2 |
| Vitamin B9 | 0.2 |
| Vitamin B12 | 0.001 |
| Vitamin C | 60 |
| Vitamin E | 10 |

TABLE 2-continued composition of formula B without resveratrol

| Ingredient | Quantity (mg) |
|---|---|
| Zinc | 7.5 |
| Manganese | 1 |
| Selenium | 0.025 |
| Copper | 1 |
| Lutein | 10 |
| Zeaxanthin | 2 |
| Fish oil | 400 |
| EPA content | 160 |
| Glutathion | 1 |

Dilutions of this composition, denoted B1, B5, B10 and B20, were produced under conditions similar to those described in point II-1: 0.115 grams of formula B in 1 mL of DMSO, then equivalent dilutions in the culture medium.

FIG. 1 illustrates the results obtained on the pathological cells, treated with the composition according to the invention (A) or the equivalent thereof without resveratrol (B).

It can be seen from this figure that on this type of cell, the presence of resveratrol causes a decrease in the expression of receptors (VEGFR1 and VEGFR2), as well as their phosphorylation:

the composition according to the invention (A) makes it possible to suppress the expression of the VEGF and of the VEGF receptors, and in a way that is dose-dependent;

the phosphorylation of the receptors present also decreases, and in a way that is dose-dependent, which indicates a reduction of activation of these receptors.

The composition according to the invention thus causes a quantitative reduction, but also qualitative reduction of the activation of the VEGF receptors in pathological cells, and consequently of neovascularization.

Insofar as the composition without resveratrol (formula B) does not enable a reduction in the expression of VEGF receptors, nor their phosphorylation (FIG. 1B), this effect would therefore be related to the presence of resveratrol.

2) Evidence of Synergy in the Composition According to the Invention

The dose-dependent effect of the composition according to the invention on pathological cells was compared to that of the R20 solution, containing only 20 μM resveratrol.

Figure 1B:
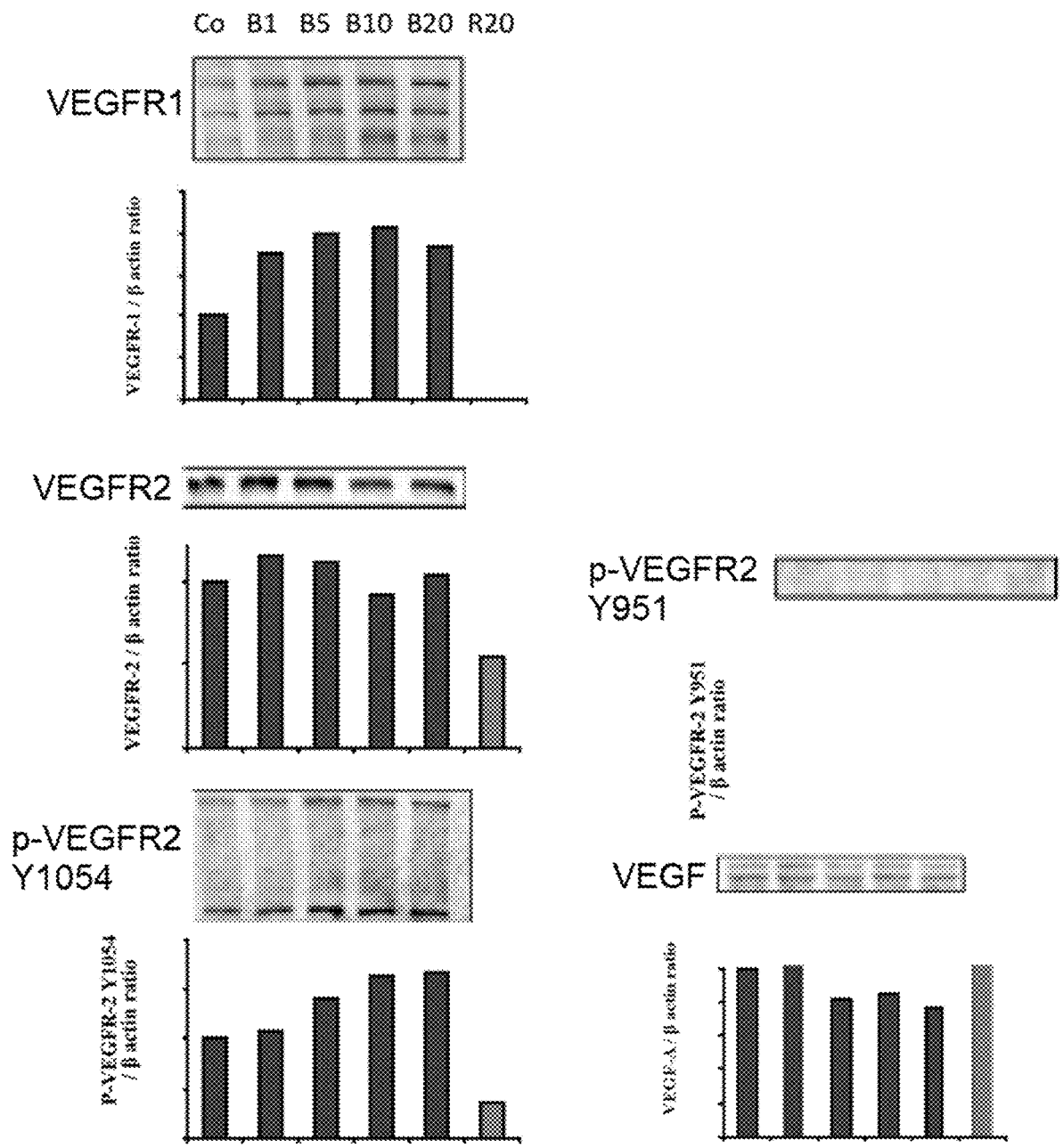

FIG. 1A shows that resveratrol alone makes it possible to reduce the expression of VEGF receptors. However, this effect is amplified in the presence of other ingredients of the composition according to the invention (compare A20 and R20).

II-3/Effect of the Composition According to the Invention on Healthy Cells

A/Protocol:

The protocol used is the same as the one described in the example II-2, except for the cells studied:

Cells studied: culture of differentiated ARPE-19 (human retinal pigment epithelium) cells.

Protocol for Obtaining Differentiated Cells:

The undifferentiated cells are seeded in T75 flasks. The cells are maintained at 37° C., and in the presence of 5% CO2 in the medium DMEM/F12 (GIBCO; 31331), completed with 10% FBS (Lonza) and 15 mM HEPES (pH 7.4; GIBCO). When the cells reach confluence, the medium is replaced by DMEM/F12 (GIBCO; 31331), completed with 1% FBS (Lonza) and HEPES (15 mM pH 7.4; GIBCO). The media were changed 2 times per week for 8 weeks.

Said cells can be equated with undamaged or healthy retinal cells.

B/Results:

1) Evidence of the Activity of the Resveratrol

FIG. 2 illustrates the effect of the composition according to the invention (A), or the equivalent thereof without resveratrol (B), on healthy cells.

Contrary to what was observed in pathological cells, the composition according to the invention (A) increases the expression of the VEGF receptors in a way that is dose-dependent. Moreover, the phosphorylation of the receptors also shows an increase. There is therefore a quantitative as well as qualitative increase of the activation, and consequently of the neovascularization of healthy cells.

Figure 2A:
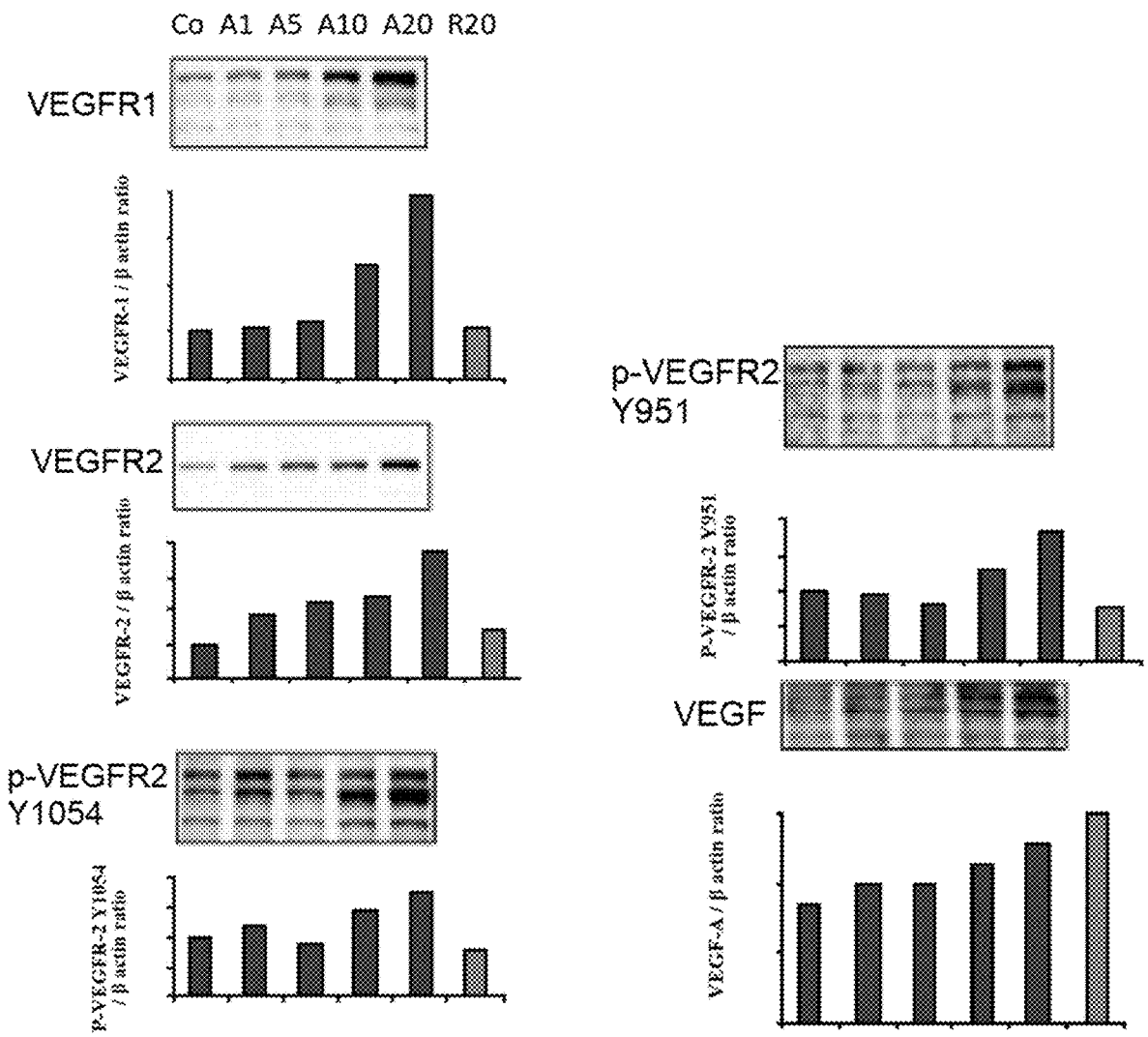
FIGS. 2A and 2B compare, in differentiated (healthy) retinal cells incubated (A) in the presence of a composition according to the invention (formula A) or (B) and in the presence of a composition similar to the one of the invention but without resveratrol (formula B), the expression of VEGFR receptors (VEGFR1 and VEGFR2) and their phosphorylation state (p-VEGF2 Y1054 and Y951), as well as VEGF, by western blot (image) and normalization by β-actin (diagram).
Figure 2B:
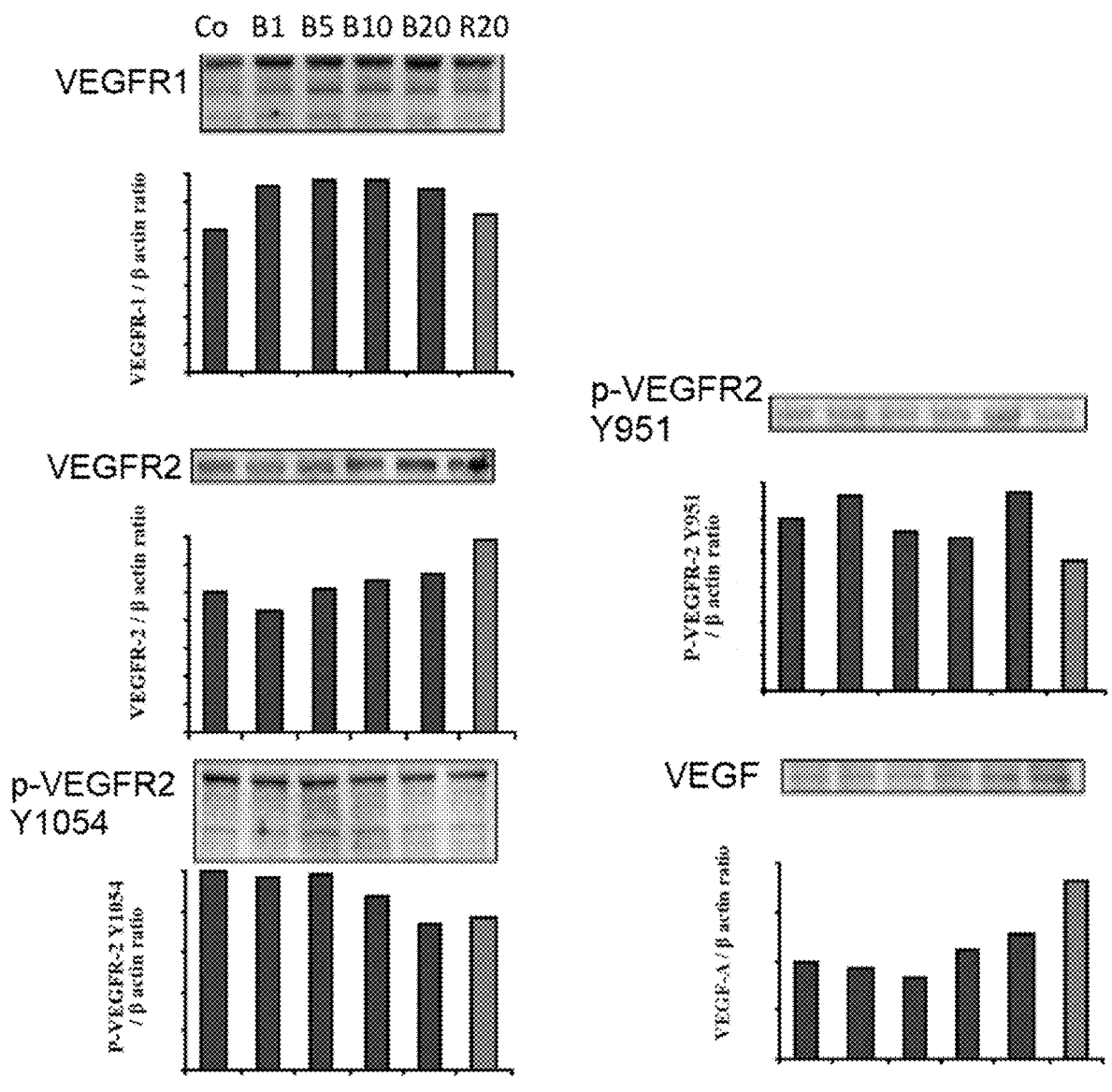

However, no effect was observed with the formulation without resveratrol (see FIG. 2: compare FIG. 2A and FIG. 2B).

It can be seen from FIG. 2 that this increase is dose-dependent and significant for the highest concentrations of resveratrol.

2) Evidence of Synergy in the Composition According to the Invention

The dose-dependent effect of the composition according to the invention on healthy cells was compared to that of a solution containing only resveratrol in the amount of 20 µM (FIG. 2, R20): this reveals that resveratrol alone at the concentration tested has no effect on healthy cells, just like the formula without resveratrol (FIG. 2B).

III/EFFECT OF THE COMPOSITION ACCORDING TO THE INVENTION IN VIVO IN THE MOUSE

In order to validate the preceding results obtained in vitro on a cellular model, experiments were performed in the animal, using C57BL/6 mice as model. In order to reproduce the symptoms of AMD, the mice (apart from the control group of mice) received an injection of 0.5 µg lipopolysaccharide (LPS) in one of the two eyes (right eye).

AMD is characterized by chronic inflammation. Lipopolysaccharides are well known for inducing local inflammation, resulting in stimulating the expression of cytokines in the damaged tissues. Since the administration of LPS is by injection and is confined to the eye, it is expected that the LPS acts only locally in the injected (right) eye, and is not diffused to other tissues, particularly into the left eye.

Prior to the injection of LPS and to test the efficacy of the different compositions, the mice received orally, once per day for 15 days, either resveratrol alone (R), or the composition A according to the invention described in table 1 (A), or the comparative composition B without resveratrol as described in table 2 (B).

Upon completion of the treatments, the retinas of the eyes of the mice are removed and the levels of expression of the VEGF, VEGF-R1, and VEGF-R2, and of the activated form (phosphorylated on tyrosine 951) of the VEGF-R2 were analyzed.

A/Protocol:

C57BL/6 mice were separated into 5 groups:

1 control group (Co) received only the carrier;

1 group (LPS) received a retro-orbital injection of 0.5 µg LPS (*E. Coli*) in the right eye on the $12^{th}$ day;

1 group (R) received, by oral administration, resveratrol alone in a dose of 35 mg/kg/day for 15 days, and 0.5 µg LPS was administered in the right eye by retro-orbital injection on the $12^{th}$ day, or 72 h before the end of the experiment;

1 group (A) received, by oral administration, the composition A from table 1 in a dose of 314.5 mg/kg/day for 15 days, and 0.5 µg LPS was administered in the right eye by retro-orbital injection on the $12^{th}$ day, or 72 h before the end of the experiment;

1 group (B) received, by oral administration, the composition B from table 2 in a dose of 314.5 mg/kg/day for 15 days, and 0.5 µg LPS was administered in the right eye by retro-orbital injection on the $12^{th}$ day, or 72 h before the end of the experiment.

At the end of the experiment, the mice are anesthetized and euthanized in order to remove the retinas from the right eye (having received the LPS injection and imitating the diseased eye) and of the left eye (imitating the healthy eye). The retinas are then lysed in order to study by Western-blot the expression of the proteins of the VEGF pathway.

In parallel, different organs were removed to verify the non-toxicity of the tested compositions.

Figure 3A:
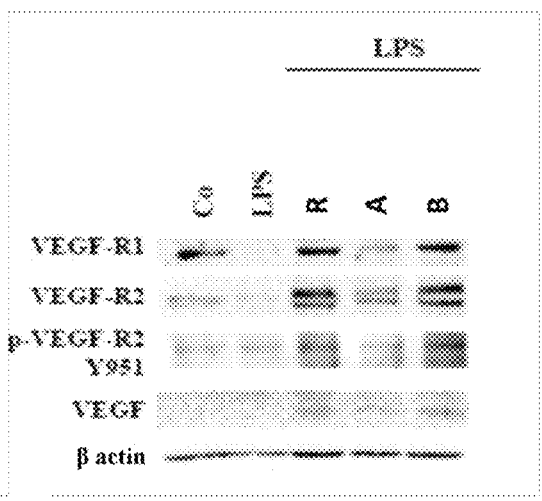
FIGS. 3A and 3B compare by western blot (A) and in diagram form after normalization by β-actin (B) the expression of VEGFR receptors (VEGFR1 and VEGFR2) and their state of phosphorylation (p-VEFG2 Y951) in the mouse eye having or not having (Co) received an injection of LPS (LPS), when they are treated with the composition according to the invention (A), with resveratrol alone (R) or with a composition without resveratrol (B).
Figure 3B:
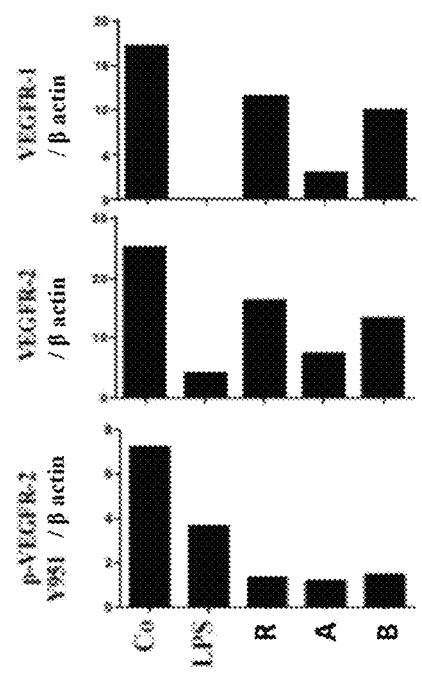

B/Results:

The results obtained for the retinas of the right eye (imitating the damaged eye) are presented in FIG. 3. The results obtained for the retinas of the left eye (imitating the healthy eye) are presented in FIG. 4.

1/Eye Treated by LPS Injection (Right):

In the right eye, it is expected that the LPS injection causes an inflammatory response, particularly the overexpression of cytokines and therefore activation of the VEGF pathway, as described by Nagineni et al. (*Aging and Disease*, 2014; 5(2): 88-100). It can be seen from FIG. 3 that the levels of expression of VEGF-R1, VEGF-R2, the presence of VEGF-R2 in phosphorylated form, and even the level of VEGF are very low in the mice labeled LPS, while a higher expression of these proteins (in comparison with the untreated control Co) was expected due to the induced inflammation. These results tend to show that treatment by 0.5 µg LPS (LPS specimen of FIG. 3) is very toxic and very poorly supported by the retinas of the mice. The small quantity of proteins is therefore explained by the toxicity of the LPS which causes cellular death and consequently the cells cannot express the VEGF receptors or secrete VEGF.

In comparison, the retinas of the right eye of the mice having received an injection of LPS but having consumed either resveratrol (R), the composition A or the composition B, show very high levels of proteins, which seems to indicate that the consumption of these products has made it possible, at least to a certain degree, to protect the cells of the retina from the toxic effect of the LPS.

Moreover, it will be noted that taking the composition A daily for 15 days causes a significant decrease in the expression of VEGF receptors such as VEGF-R1, VEGF-R2 and activated phospho-VEGF-R2 Y951 form thereof compared to the control mice, and this is more significant than what is observed with the composition B without resveratrol or with resveratrol alone (R). These results, therefore, are coherent with what was observed in vitro in FIG. 1, showing the value of the composition according to the invention for inhibiting more effectively the activation pathway of the VEGF receptors in a pathological, inflammatory context.

Figure 4A:
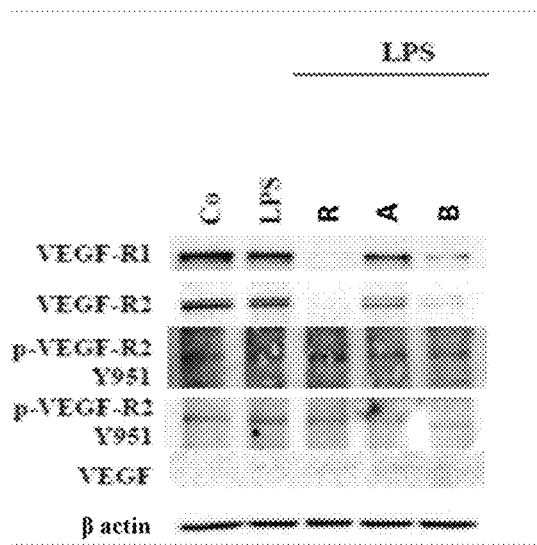
FIGS. 4A and 4B compare by western blot (A) and in diagram form after normalization by β-actin (B) the expression of VEGFR receptors (VEGFR1 and VEGFR2) and their state of phosphorylation (p-VEFG2 Y951) in the eye of the Control mouse (Co) or having received an injection of LPS (LPS), when they are treated with the composition according to the invention (A), with resveratrol alone (R) or with a composition without resveratrol (B).
Figure 4B:
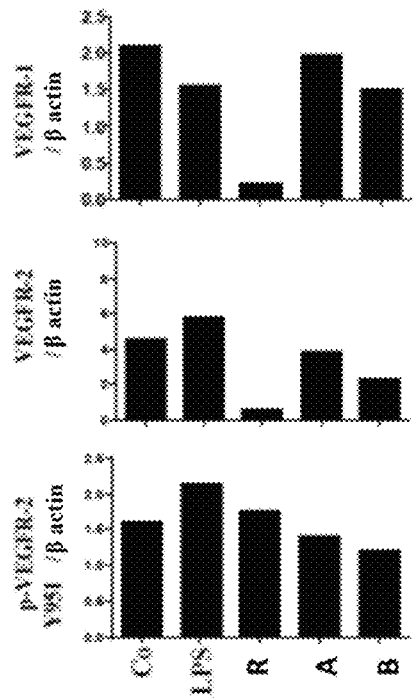

2/Contralateral Eye not Treated by Injection of LPS (Left):

The results obtained with the retinas of the left eye, not having had contact with the LPS and imitating a healthy eye, are shown in FIG. 4.

The data obtained show that the effect of resveratrol alone (R), as expected, is to decrease the expression of VEGF-R1 and VEGF-R2. Significantly, the composition A according to the invention makes it possible to maintain a level of VEGF-R1, VEGF-R2 and of the activated phospho-VEGF-R2 Y951 form, comparable to the control mice (Co). There is a lesser effect for the composition B without resveratrol. In other words, and as observed in vitro (FIG. 2), the combination of resveratrol and vitamins, trace elements, carotenoids and omega-3 fatty acids of the composition according to the invention has a synergistic effect in comparison with resveratrol alone and the composition B.

It can be seen from the results above that the composition A is capable of decreasing the VEGF-R activation pathway in diseased retinal cells but is also capable of maintaining a normal level of functioning of said pathway in normal retinas, which is essential for maintaining sufficient blood flow to the retina and avoiding the degeneration processes.

Thus, and contrary to resveratrol alone, the composition A can advantageously be administered to subjects in whom only one of the two eyes is damaged, with benefit to the damaged eye without affecting the healthy eye.

CONCLUSIONS

Surprisingly and for the first time in the field of ophthalmology, in relation to retinal cells, it has been shown that a composition according to the invention containing resveratrol has a differential action at VEGFR receptors necessary for neovascularization, depending on the type of cells: repression in pathological cells and no repression, and even a reverse effect, in healthy cells.

Thus, the resveratrol in the context of a composition according to the invention would make it possible to reestablish a balance within the "deficient" cells but would not modify in any way, and would even "keep fit" the healthy cells by means of the supplemental contribution of the essential elements provided by blood circulation.

In the same way, in patients at risk, the administration of the composition A would make it possible to prevent the appearance of the symptoms, allowing the first "anomalies" to be treated by preserving the health potential while waiting for the appearance of anomalies. Indeed, the retinal cells will still receive the supply of necessary oxygen, nutrients and vitamins via physiological blood flow supported by a physiological level of VEGF, which will not decrease as could be the case with resveratrol alone.

What is claimed is:

1. A method of treating an eye pathology caused by an overexpression of a vascular endothelial growth factor (VEGF) pathway in a subject in need thereof, the method comprising:
    administering to the subject a daily dose composition consisting of:
        120 mg to 240 mg of vitamin C;
        10 mg to 500 mg of vitamin E;
        5 mg to 100 mg of zinc;
        0.2 mg to 10 mg of copper;
        2 mg to 50 mg of the lutein;
        0.5 mg to 10 mg of zeaxanthin;
        fish oil comprising:
            172 mg to 380 mg of EPA; and
            190 to 366 mg of DHA; and
        30 to 200 mg of resveratrol,
        wherein said eye pathology is selected from the group consisting of exudative age-related macular degeneration (AMD), retinal venous occlusion, macular edema, diabetic macular edema, myopia, diabetic retinopathy, neovascular glaucoma, and corneal neovascularization.

2. The method according to claim 1, wherein the composition consists of:
    120 mg to 240 mg of vitamin C;
    30 mg of vitamin E;
    12.5 mg of zinc;
    1 mg of copper;
    10 mg of the lutein;
    2 mg of zeaxanthin;
    fish oil comprising:
        172 mg to 380 mg of EPA; and
        190 to 366 mg of DHA; and
    30 mg of resveratrol.

3. The method according to claim 1, wherein said subject is suffering from symptoms of said pathology only in one eye.

4. The method according to claim 1, wherein the composition is administered orally.

5. The method according to claim 1, wherein the composition is formulated as a capsule, a tablet, or a pill.

* * * * *